US 008070721 B2

(12) United States Patent
Kakish et al.

(10) Patent No.: US 8,070,721 B2
(45) Date of Patent: Dec. 6, 2011

(54) AUTO-DISABLE DEVICE FOR SYRINGES

(75) Inventors: Amer F. A. Kakish, Abu Dhabi (AE); Osama Y. T. Al Omari, Abu Dhabi (AE)

(73) Assignee: ABU Dhabi National Industrial Projects Co. (GC)

( * ) Notice: Subject to any disclaimer, the term of this patent is extended or adjusted under 35 U.S.C. 154(b) by 28 days.

(21) Appl. No.: 12/184,302

(22) Filed: Aug. 1, 2008

(65) Prior Publication Data

US 2010/0030146 A1 Feb. 4, 2010

(51) Int. Cl.
*A61M 5/00* (2006.01)
(52) U.S. Cl. .......................................... 604/110
(58) Field of Classification Search .................. 604/110, 604/533
See application file for complete search history.

(56) References Cited

U.S. PATENT DOCUMENTS

| | | | |
|---|---|---|---|
| 2,902,995 A | 9/1959 | Loper | |
| 3,491,757 A | 1/1970 | Arce | |
| 4,233,975 A | 11/1980 | Yerman | |
| 5,045,063 A | 9/1991 | Spielberg | |
| 5,120,314 A | 6/1992 | Greenwood | |
| RE34,335 E * | 8/1993 | Butler et al. | 604/110 |
| 5,478,321 A | 12/1995 | Kimber | |
| 5,613,951 A * | 3/1997 | Meyer et al. | 604/110 |
| 5,814,017 A | 9/1998 | Kashmer | |
| 6,013,056 A | 1/2000 | Pettersen | |
| 6,165,153 A * | 12/2000 | Kashmer | 604/110 |
| 6,267,749 B1 | 7/2001 | Miklos et al. | |
| 6,287,279 B1 | 9/2001 | Siekmann | |
| 6,840,291 B2 * | 1/2005 | Caizza et al. | 141/25 |
| 7,056,301 B2 | 6/2006 | Liu | |
| 7,090,657 B2 | 8/2006 | Tang | |
| 2003/0073959 A1 | 4/2003 | Koska | |
| 2006/0084916 A1 | 4/2006 | Lo | |
| 2007/0270743 A1 | 11/2007 | Ackerman | |

FOREIGN PATENT DOCUMENTS

| | | |
|---|---|---|
| EP | 1 842 570 | 10/2007 |
| WO | WO 92/04064 A | 3/1992 |
| WO | WO 97/26933 A1 | 1/1997 |
| WO | 2006/066336 * | 6/2006 |
| WO | WO 2006/066366 A | 6/2006 |
| WO | WO 2007/028296 | 3/2007 |

OTHER PUBLICATIONS

International Search Report, Abu Dhabi National Industrail Projects Co., et al., PCT/IB2008/003447, Apr. 22, 2009, 5 pages.

* cited by examiner

*Primary Examiner* — Theodore Stigell
(74) *Attorney, Agent, or Firm* — McKee, Voorhees & Sease, P.L.C.

(57) ABSTRACT

An auto-disable device for use with a sterile single use hypodermic syringe has a barrel adapter configured to attach to the outlet end of the syringe barrel, external to the barrel. A needle hub holding a hypodermic needle is affixed to the barrel adapter, the barrel adapter and the needle hub forming an assembly having a cavity with a passage for the flow of liquid through the device. An elastically-deformable sealing ring and a moveable sealing member having a head and a shaft are positioned in the cavity. The sealing member is moveable within the cavity. The ring and moveable sealing member are configured to form a seal, after a single use of the syringe, against a flow of liquid into the syringe for refilling of the syringe.

7 Claims, 3 Drawing Sheets

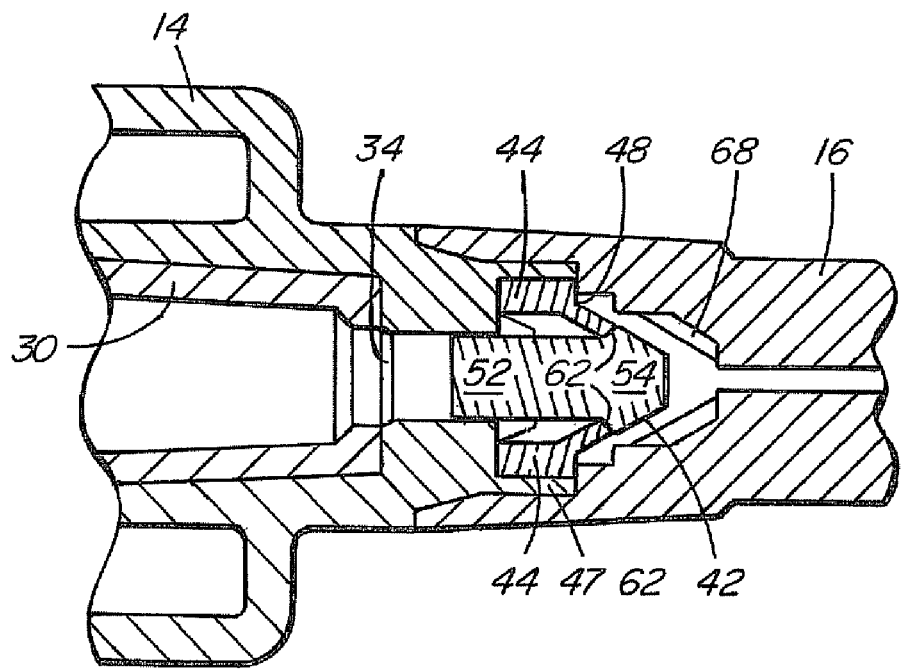
FIG. 2
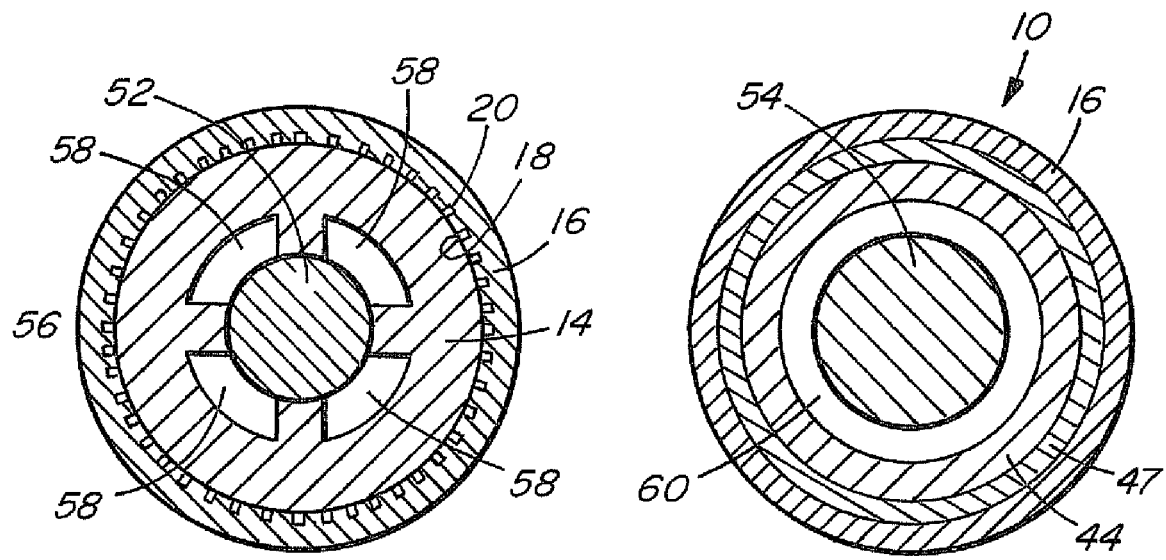
FIG. 3
FIG. 4

AUTO-DISABLE DEVICE FOR SYRINGES

FIELD OF THE INVENTION

The invention pertains to devices for preventing the reuse of sterile single use syringes.

BACKGROUND OF THE INVENTION

It is known to provide a hypodermic syringe with a device that prevents it from being used more than a single time. Such devices are typically installed in the syringe barrel between the piston and the outlet end of the barrel and prevent the syringe from being refilled. An example is shown in Meyer et al., U.S. Pat. No. 5,613,951. Since the devices are internal to the syringe barrel, either the barrel is sized and configured to fit a device of a specific diameter, or the devices are made in different sizes to fit the barrels of syringes of different sizes. Further, because of the requirement that the devices fit inside the barrel, there is a practical lower limit to the size of syringe in which such devices can be installed.

SUMMARY OF THE INVENTION

The invention provides an anti-reuse device for a syringe, the device being external to the syringe. The device is an auto-disable device that is automatically activated and remains effective from the time that the injection of liquid from the syringe has commenced.

The auto-disable device comprises an assembly made of a barrel adapter and a needle hub. The barrel adapter is configured to attach to the outlet end of the barrel of a syringe, the attachment being external to the barrel. The needle hub is affixed to the barrel adapter and has a fixed hypodermic needle, which can be of various sizes as required. The assembly has a cavity with a passage for the flow of liquid from the assembly inlet to the needle. The device includes an elastically-deformable sealing ring in the cavity having an opening therein. A sealing member in the cavity has a head and a shaft, the sealing member being moveable in the cavity in a longitudinal direction from a first position in which the head of the sealing member is on a side of the ring facing the inlet of the assembly to a second position in which the head of the sealing member is on a side of the sealing ring facing the needle. The sealing ring is configured to stop movement of the sealing member from the second position to the first position and to form a seal with the head, when the sealing member is in the second position, against a flow of liquid in the direction of the inlet end of the assembly.

Being external to the barrel of the syringe, the auto-disable device can be used with syringes of different sizes. There are therefore no practical limitations to the syringe barrel dimensions. The device can be conveniently attached to syringes that are intended for single use, to convert them into auto-disable syringes, provided that the outer luer cone of the syringe barrel is adjusted to permit locking of the device to the barrel. The device disables the syringe by means of the expulsion of liquid from the syringe in the course of doing an injection, without a further action to disable the syringe. Thus the term, "auto-disable."

The auto-disable device, which includes the needle, can be assembled with the syringe at the factory and delivered as a unit, or, alternatively, the device can be provided separate from the syringe and be attached to it by a medical practitioner prior to use.

These and other features of the invention will be apparent from the following description and drawings of the preferred embodiments.

BRIEF DESCRIPTION OF THE DRAWINGS

FIG. 2 is a partial longitudinal cross-sectional view of the auto-disable device, with the moveable sealing member in the sealing position.

FIG. 3 is a cross-sectional view on the line 3-3 of FIG. 1.

FIG. 4 is a cross-sectional view on the line 4-4 of FIG. 1.

DESCRIPTION OF THE PREFERRED EMBODIMENTS

Figure 1:
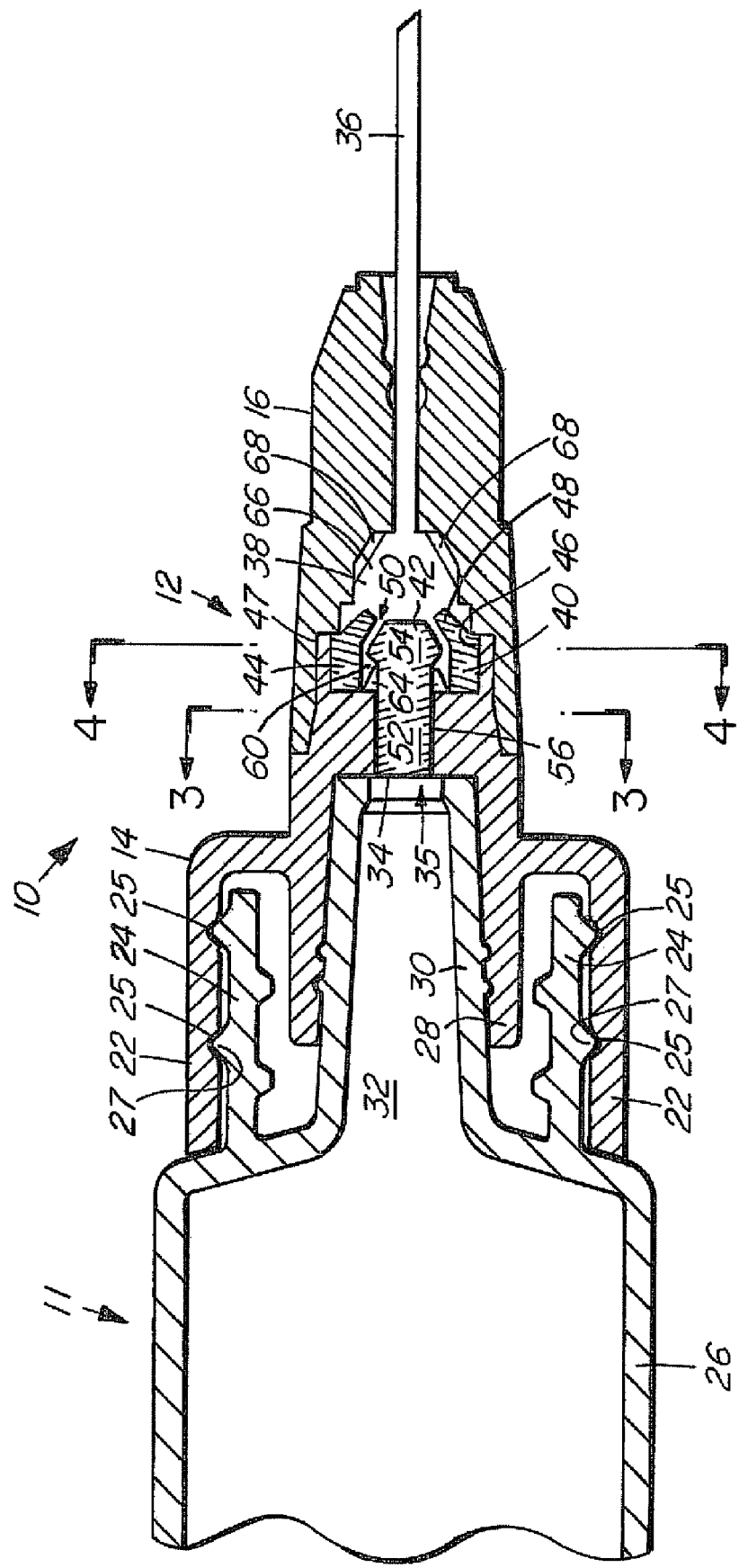
FIG. 1 is a longitudinal cross-sectional view of the auto-disable device of the invention attached to a sterile single use hypodermic syringe.
Figure 5A:
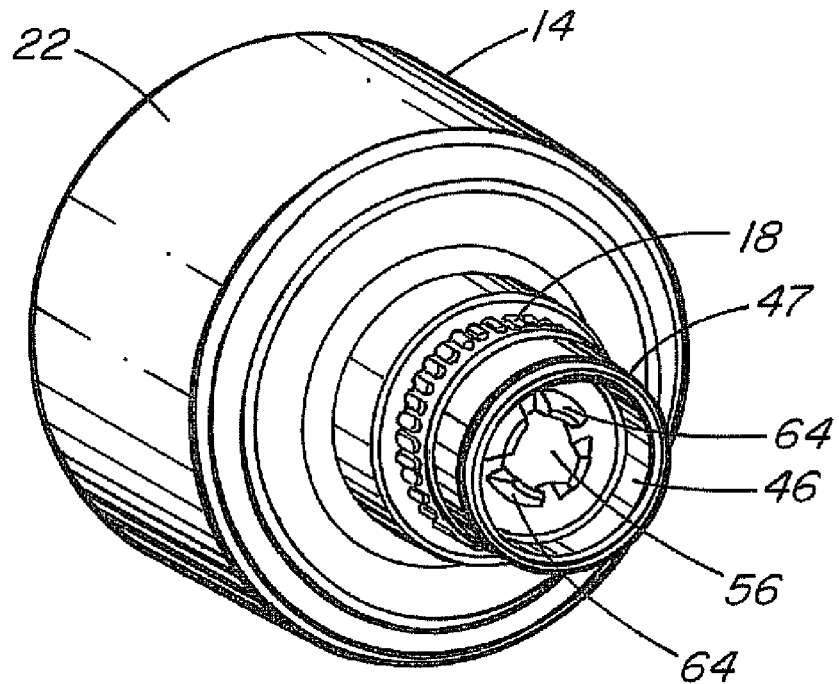
FIGS. 5A and 5B are perspective views of the barrel adapter portion of the auto-disable device assembly.
Figure 5B:
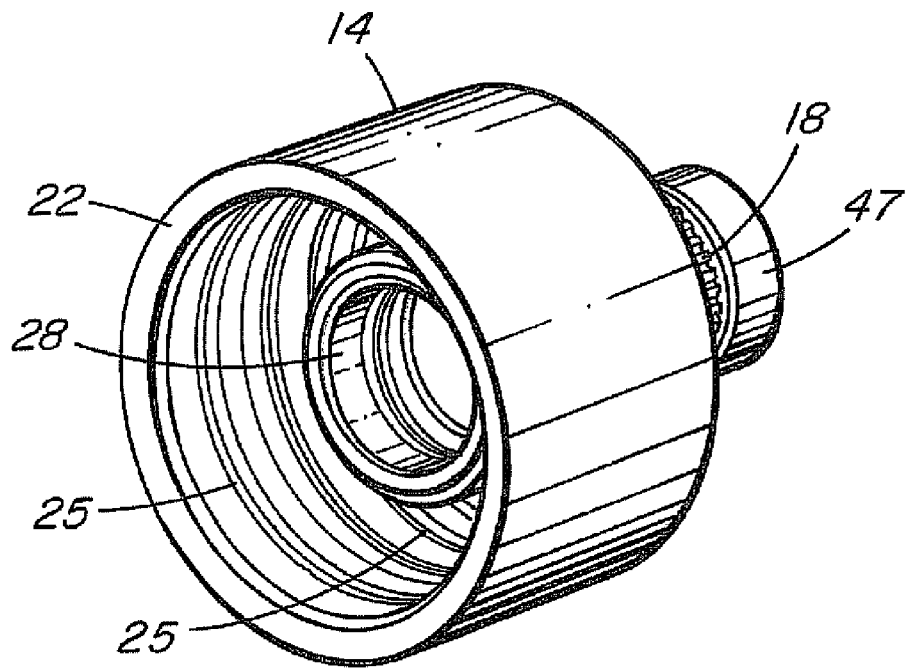

The auto-disable device 10 is shown in FIG. 1 attached to a sterile single use hypodermic syringe 11. The device 10 has an assembly 12 formed of a barrel adapter 14 and a needle hub 16. The barrel adapter and hub attach securely together by means of circumferentially-disposed ribs 18 on the barrel adapter which interfit tightly with mating grooves 20 on the needle hub. A hypodermic needle 36 is affixed to the distal end of the needle hub.

The barrel adapter 14 has an outer circumferential wall 22 for locking engagement with a luer lock cone 24 of the barrel 26 of the syringe. A number of circumferential grooves 25 on the inner surface of the wall 22 interfit with circumferential ridges 27 on the outer surface of the luer lock cone 24 of the barrel, providing a snap-on fit. The barrel adapter 14 has an inner circumferential wall 28 for mating engagement with the outlet cone 30 at the outlet end 32 of the barrel. The barrel adapter 14 has an inlet 34 at an inlet end 35 thereof. The inlet 34 aligns with the barrel outlet at the distal end of the barrel outlet cone 30.

The assembly 12 has a cavity 38 extending longitudinally therethrough from the inlet 34 to the needle 36.

A sealing ring 40 and a moveable sealing member 42 are positioned in the cavity 38. The sealing ring has an annular base portion 44 which fits snugly against the inner surface 46 of the ring-retaining portion 47 of the barrel adapter, and an elastically-deformable, inwardly-extending sealing portion 48 having an opening 50 therein. The moveable sealing member 42 has a shaft portion 52 and a head portion 54.

The barrel adapter 14 has a cylindrical guiding portion 56 which receives the shaft portion 52 of the sealing member 42. Four channels 58, best seen in FIG. 3, extend along the sides of the guiding portion 56 between the inlet 34 of the barrel adapter and a section 60 of the cavity adjacent to the sealing ring. These channels permit the flow of liquid from the inlet 34 to the section 60 of the cavity 38 and also enable syringe filling.

The head 54 of the moveable sealing member 42 has a diameter larger than the diameter of the opening 50 of the sealing ring 40. The sealing portion 48 of the sealing ring is angled in the direction of the needle 36 and is elastically deformable such that the head 54 of the moveable sealing member can pass through the opening 50 in the direction of the needle under the pressure of liquid caused when the piston in the syringe is moved in the direction of the needle.

The barrel adapter 14 has four guiding lugs 64 which extend into the cavity section 60 adjacent to the guiding portion 56 of the barrel adapter. These lugs support the moveable sealing member 42 in its movement in the direction of the needle.

The cavity 38 includes a section 66 within the needle hub into which the head 54 of the moveable sealing member 42 moves. Channels 68 are provided in the wall of the cavity section 66, adjacent to the inward end of the needle, permitting the flow of liquid past the head 54 of the sealing member 42 when the head is in the cavity section 66.

For the initial filling of the syringe, the sealing member 42 is in a position on the side of the sealing member facing the inlet 34 of the auto-disable device 10. Liquid can then be drawn into the barrel of the syringe by movement of the syringe piston in the direction away from the needle, the liquid passing through the needle into the cavity 38, through the opening 50 in the sealing ring 40, through the channels 58 in the barrel adapter 14 and out through the inlet 34 into the syringe barrel 26. When the syringe piston is then pressed in the direction of the needle to deliver the liquid, the liquid flows from the barrel into the inlet 34 and through the channels 58, pressing against the inlet side of the sealing portion 48 of the ring 40 and against the inlet end of the moveable sealing member 42. This causes the opening 50 of the sealing ring 40 to enlarge and permit the head 54 of the moveable sealing member to be pushed through the opening and also permit the liquid to flow through the opening 50 in the direction of the needle, through the channels 68 and out through the needle.

Movement of the moveable sealing member 42 in the opposite direction is stopped by the engagement of the sealing portion 48 of the ring 40 with the head 54 of the moveable sealing member. As shown in FIG. 2, the sealing portion 48, and more specifically its sealing surface 62 around the opening 50, seals against the head 54, stopping any flow of fluid in the direction of the inlet 34 of the assembly.

The components of the auto-disable device may be made of any suitable materials. Such suitable materials include polystyrene, polypropylene or polyethylene for the barrel adapter 14 and for the needle hub 16, acrylonitrile butadiene styrene (ABS) for the moveable sealing member 42, thermoplastic elastomer (TPE) for the sealing ring 40 and stainless steel for the needle.

Although the invention has been described in terms of specific embodiments, it is not intended that the invention be limited to those embodiments. Various modifications within the scope of the invention will be apparent to those skilled in the art. For example the barrel adapter can be a luer slip barrel adapter, or be shaped to attach to various kinds of fittings on syringe barrels. The scope of the invention is defined by the claims that follow.

What is claimed is:

1. An auto-disable device for connection externally to a sterile single use hypodermic syringe to prevent refilling of the syringe after use, the device comprising:

(a) a barrel adapter configured to attach to an outlet of a barrel of the syringe, said attachment being external to the barrel and such that an inlet of the barrel adapter is in fluid communication with the outlet of the barrel;
   (b) a needle hub affixed to the barrel adapter and having a hypodermic needle affixed thereto;
   (c) the barrel adapter and the needle hub forming an assembly having a longitudinal axis, the assembly having a cavity with a passage for the flow of a liquid from the inlet of the barrel adapter to the needle, the cavity having a section thereof that is within the needle hub and outside the barrel adapter, the barrel adapter having a cylindrical ring-retaining portion at an end thereof that engages the needle hub;
   (d) an elastically-deformable sealing ring in the cavity, the sealing ring having an annular base portion and an inwardly-extending sealing portion having an opening therein, the annular base portion being fitted into the ring-retaining portion of the barrel adapter, the needle hub abutting against the ring-retaining portion of the barrel adapter and against the sealing ring;
   (e) a sealing member in the cavity having a head and a shaft, the sealing member being moveable in the cavity in a longitudinal direction from a first position in which the head of the sealing member is on a side of the sealing portion of the ring facing the inlet of the barrel adapter to a second position in which the head of the sealing member is on a side of the sealing portion of the ring facing the needle and within the section of the cavity that is within the needle hub; and
   (f) the sealing portion of the ring being configured to stop movement of the sealing member from the second position to the first position and to form a seal with the head, when the sealing member is in the second position, against a flow of liquid in the direction from the needle to the inlet of the barrel adapter.

2. An auto-disable device according to claim 1, wherein the barrel adapter is a luer lock barrel adapter.

3. An auto-disable device according to claim 1, wherein the barrel adapter is a luer slip barrel adapter.

4. An auto-disable device according to claim 1, further comprising interlocking ribs and grooves to attach the barrel adapter and needle hub together.

5. An auto-disable device according to claim 1, wherein the barrel adapter includes an outer circumferential wall for locking engagement with a luer cone of the syringe barrel.

6. An auto-disable device accordingly to claim 1, wherein the barrel adapter includes an inner circumferential wall for mating engagement with an outlet cone of the syringe barrel.

7. An auto-disable device according to claim 1, in combination with the syringe, the barrel adapter being attached to the outlet of the barrel, external to the barrel, with the inlet of the barrel adapter in fluid communication with the outlet of the barrel.

* * * * *